(12) United States Patent
Shkolnikov (10) Patent No.: US 8,909,497 B1
(45) Date of Patent: Dec. 9, 2014

(54) SYSTEM AND METHOD FOR FALL DETECTION

(75) Inventor: Mark Shkolnikov, Herndon, VA (US)

(73) Assignee: Keynetik, Inc., Herndon, VA (US)

( * ) Notice: Subject to any disclaimer, the term of this patent is extended or adjusted under 35 U.S.C. 154(b) by 291 days.

(21) Appl. No.: 13/080,580

(22) Filed: Apr. 5, 2011

Related U.S. Application Data (60) Provisional application No. 61/321,170, filed on Apr. 6, 2010.

(51) Int. Cl.
*G01P 15/00* (2006.01)
*A61B 5/00* (2006.01)
*A61B 5/11* (2006.01)
*G08B 21/04* (2006.01)

(52) U.S. Cl.
CPC ............... *G01P 15/00* (2013.01); *A61B 5/7282* (2013.01); *A61B 5/1117* (2013.01); *G08B 21/0438* (2013.01); *A61B 5/1121* (2013.01); *G08B 21/0446* (2013.01); *A61B 5/1116* (2013.01)
USPC ........ 702/141; 702/150; 340/573.1; 340/669; 600/595

(58) Field of Classification Search
CPC .... G01P 15/00; A61B 5/1116; A61B 5/1117; A61B 5/1121; A61B 5/7282; G08B 21/0438; G08B 21/0446
USPC ......... 702/141, 150; 340/573.1, 669; 600/595
See application file for complete search history.

(56) References Cited

U.S. PATENT DOCUMENTS

| | | | |
|---|---|---|---|
| 4,492,235 A * | 1/1985 | Sitrick | 600/518 |
| 5,247,466 A * | 9/1993 | Shimada et al. | 702/141 |
| 6,433,690 B2 | 8/2002 | Petelenz et al. | |
| 6,997,882 B1 | 2/2006 | Parker et al. | |
| 7,382,567 B2 | 6/2008 | Liao et al. | |
| 7,961,109 B2 * | 6/2011 | Jang et al. | 340/573.1 |
| 8,206,325 B1 * | 6/2012 | Najafi et al. | 600/595 |
| 2006/0001545 A1 | 1/2006 | Wolf | |
| 2006/0152842 A1 | 7/2006 | Pasolini et al. | |
| 2006/0279426 A1 | 12/2006 | Bonnet et al. | |
| 2006/0282021 A1 | 12/2006 | De Vaul et al. | |
| 2008/0129518 A1 * | 6/2008 | Carlton-Foss | 340/573.1 |
| 2008/0252445 A1 | 10/2008 | Kolen | |
| 2008/0255795 A1 * | 10/2008 | Shkolnikov | 702/141 |
| 2009/0048540 A1 | 2/2009 | Otto et al. | |
| 2009/0224925 A1 | 9/2009 | Gannot et al. | |
| 2009/0292227 A1 | 11/2009 | Scholten et al. | |
| 2009/0322540 A1 * | 12/2009 | Richardson et al. | 340/573.7 |
| 2010/0121226 A1 | 5/2010 | Ten Kate et al. | |
| 2010/0121603 A1 | 5/2010 | Nyan et al. | |
| 2010/0286567 A1 | 11/2010 | Wolfe et al. | |
| 2011/0246123 A1 * | 10/2011 | DelloStritto et al. | 702/141 |

FOREIGN PATENT DOCUMENTS

| | | |
|---|---|---|
| GB | 2401466 | 11/2004 |
| WO | 2010105045 | 9/2010 |

* cited by examiner

*Primary Examiner* — Mohamed Charioui
*Assistant Examiner* — John Kuan
(74) *Attorney, Agent, or Firm* — Lieberman & Brandsdorfer, LLC (57) ABSTRACT

Embodiments of the invention relate to spectrally and spatially dissecting accelerometer data from a signal of a motion sensor. Data received from the dissected signal is reduced to statistical averages for selected frequency bands and spatial dimensions. A time segment subject over which the signal was acquired is segmented so that the dissected signal may be evaluated per the segmentation of the time. Change of orientation towards gravity of the sensor is analyzed with respect to a change of orientation from a before impact segment to an after impact segment. The analyzed change in orientation value with respect to a threshold is a factor in determination of a fall of a body to which the sensor is attached.

21 Claims, 7 Drawing Sheets

SYSTEM AND METHOD FOR FALL DETECTION

CROSS REFERENCE TO RELATED APPLICATION(S)

This is a non-provisional utility patent application claiming benefit of the filing date of U.S. Provisional Patent Application Ser. No. 61/321,170, filed Apr. 6, 2010, and titled "Fall Detection Algorithm for Belt—and Pendant-worn Mobile Personal Emergency Response Systems," which is hereby incorporated by reference.

BACKGROUND

This invention relates to a sensor and an associated algorithm and tools to detect when a person has fallen. More specifically, the invention relates to evaluating sensor data with respect to characteristics of the fall to accurately determine when the fall has taken place.

The proliferation of motion and other types of sensors enables new applications that take advantage of data gathered from the sensors. It is known that when people are old or ill the aspect of falling can be dangerous. A lot of times, these people are alone, and once they have fallen they are in need of assistance but do not have the ability to obtain the assistance. At the same time it is important to differentiate between a fall and a fall-like event. Without such differentiation, the sensor will yield a significant quantity of false—positive data, which may unnecessarily burden emergency response personnel.

Many industry fall detection solutions detect Low G ("weightlessness") as an indicator that a body is being pulled down by gravity. It is very appealing because the pull can be detected just as a change of a motion vector magnitude, so the device can be in any orientation towards gravity. However, as we realized collecting test data, Low G is also present in many normal everyday life activities. Virtually any energetic action may contain Low G periods. It is seen in walking, sitting, missing a step, even rising up. Low G can also be masked by rotations that happen in falls. There is an important benefit from not using the Low G: the requirement for accelerometer resolution can be substantially reduced.

All falls occur for one reason: loss of support which in turn can be a result of going out of balance or structural collapse of the support. Both can happen for many reasons. In an accident a person can be pushed out of balance. In a normal life somebody can just exceed their ability to keep the balance while going through standard everyday routings, trips, or slips. Elderly people are balance-challenged for age related reasons. Regardless of the basis for the fall, there is a need to accurately determine when a fall has occurred so that assistance can be provided when necessary.

BRIEF SUMMARY

This invention comprises a method, system, and article for evaluation of sensor data for a sensor attached to a body, and more specifically for detecting a fall of the body.

In one aspect of the invention, a system is provided with tools to support fall detection. The system includes a sensor attached to a body, with the sensor configured to acquire sensory data. A tool is provided in communication with the sensor. More specifically, the tool detects when the body has fallen in accordance with the acquired sensory data. The tool is further provided with elements to support the fall detection. These elements include an orientation manager, an impact manager, and an analyzer. The orientation manager extracts orientation data from the acquired sensory data. The impact manager extracts impact data from the acquired sensory data. The analyzer separates a time segment associated with the impact into at least three distinct and sequential time segments. More specifically, the time segments include a before impact segment, an impact segment, and an after impact segment. The analyzer analyzes change of orientation of the body towards gravity. Specifically, the analyzer analyzes a difference of orientation from the before impact segment and the after impact segment. Based upon the difference analyzed, a fall detection manager in communication with the analyzer compares the analyzed change of orientation data with a threshold value to determine fall of the body.

In a further aspect of the invention, a method is provided for detecting occurrence of a fall. Sensory data is received from a sensor attached to a body, and a fall is detected in accordance with the acquired sensory data. The fall detection includes: extracting body orientation data from the acquired sensory data, and extracting impact data from the acquired sensory data. Following the data extractions, a time segment associated with the impact is separated into at least three distinct and sequential time segments. The three segments include a before impact segment, an impact segment, and an after impact segment. Change of orientation of the body towards gravity is analyzed, with the analysis including a difference of orientation from the before impact segment and the after impact segment. Based upon the analysis, a fall is detected responsive to a relationship of the analyzed change of orientation data to a threshold value.

In an even further aspect of the invention, a computer program product is provided for use with a sensor attached to a body. The sensor acquires sensory data. The computer program product includes a computer readable storage medium having computer readable program code embodied thereon. The computer readable program code is provided to receive sensory data from the sensor, and to detect a fall of the body in accordance with the acquired sensory data. The detection code includes extracting orientation data from the acquired sensory data, and extracting impact data from the acquired sensory data. Code is further provided to separate a time segment associated with an impact into at least three distinct and sequential time segments. These segments include a before impact segment, an impact segment, and an after impact segment. Change of orientation of the body towards gravity is analyzed, with the analysis including a difference of orientation from the before impact segment and the after impact segment. Code is further provided to detect a fall responsive to a relationship of the analyzed change of orientation data to a threshold value Other features and advantages of this invention will become apparent from the following detailed description of the presently preferred embodiment of the invention, taken in conjunction with the accompanying drawings.

BRIEF DESCRIPTION OF THE SEVERAL VIEWS OF THE DRAWINGS

The drawings referenced herein form a part of the specification. Features shown in the drawings are meant as illustrative of only some embodiments of the invention, and not of all embodiments of the invention unless otherwise explicitly indicated. Implications to the contrary are otherwise not to be made.

DETAILED DESCRIPTION

It will be readily understood that the components of the present invention, as generally described and illustrated in the Figures herein, may be arranged and designed in a wide variety of different configurations. Thus, the following detailed description of the embodiments of the apparatus, system, and method of the present invention, as presented in the Figures, is not intended to limit the scope of the invention, as claimed, but is merely representative of selected embodiments of the invention.

The functional unit(s) described in this specification have been labeled as managers and an analyzer. A functional unit(s) may be implemented in programmable hardware devices such as field programmable gate arrays, programmable array logic, programmable logic devices, or the like. The functional unit(s) may also be implemented in software for processing by various types of processors. An identified functional unit(s) of executable code may, for instance, comprise one or more physical or logical blocks of computer instructions which may, for instance, be organized as an object, procedure, function, or other construct. Nevertheless, the executables of an identified functional unit(s) need not be physically located together, but may comprise disparate instructions stored in different locations which, when joined logically together, comprise the functional unit(s) and achieve the stated purpose of the manager.

Indeed, a functional unit(s) of executable code could be a single instruction, or many instructions, and may even be distributed over several different code segments, among different applications, and across several memory devices. Similarly, operational data may be identified and illustrated herein within the functional unit(s), and may be embodied in any suitable form and organized within any suitable type of data structure. The operational data may be collected as a single data set, or may be distributed over different locations including over different storage devices, and may exist, at least partially, as electronic signals on a system or network.

Reference throughout this specification to "a select embodiment," "one embodiment," or "an embodiment" means that a particular feature, structure, or characteristic described in connection with the embodiment is included in at least one embodiment of the present invention. Thus, appearances of the phrases "a select embodiment," "in one embodiment," or "in an embodiment" in various places throughout this specification are not necessarily referring to the same embodiment.

Furthermore, the described features, structures, or characteristics may be combined in any suitable manner in one or more embodiments. In the following description, numerous specific details are provided, such as examples of a profile manager, a hash manager, a migration manager, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

The illustrated embodiments of the invention will be best understood by reference to the drawings, wherein like parts are designated by like numerals throughout. The following description is intended only by way of example, and simply illustrates certain selected embodiments of devices, systems, and processes that are consistent with the invention as claimed herein.

A method and system are provided to separate the act of falling into three distinct time segments, and to analyze a change in body orientation with respect to these three time segments. More specifically, the time segments are sequential in nature and support a granular application to a mathematical evaluation of the fall process. In one embodiment, a tool is employed to learn the true vertical of a body associated with the before impact segment. The true vertical of the body represents the alignment of the sensor towards gravity when the body is fully erect. In one embodiment, the true vertical is a real-time application associated with movement of the sensor. Accordingly, by applying true vertical as a measurement to the before impact time segment, accuracy of the fall determination is enhanced.

A process for detecting and evaluating impact and fall, as well as the tools employed for the detection and evaluation are provided. At the outset it should be noted that sensors employed for the detection are commonly attached to a body or placed within an article of clothing worn by a user, or in an accessory attached to the user, such as a pendant. Data relied upon for fall detection includes data associated with an impact of the sensor followed by a substantially horizontal orientation of the sensor. Both impact and orientation extraction are intelligent functions. The impact detection determines a cumulative effect of an impact, including allowing for accounting of an overall energy of the fall when a person may have first touched the ground, e.g. with hands, then knees, and finally with the torso.

Figure 1:
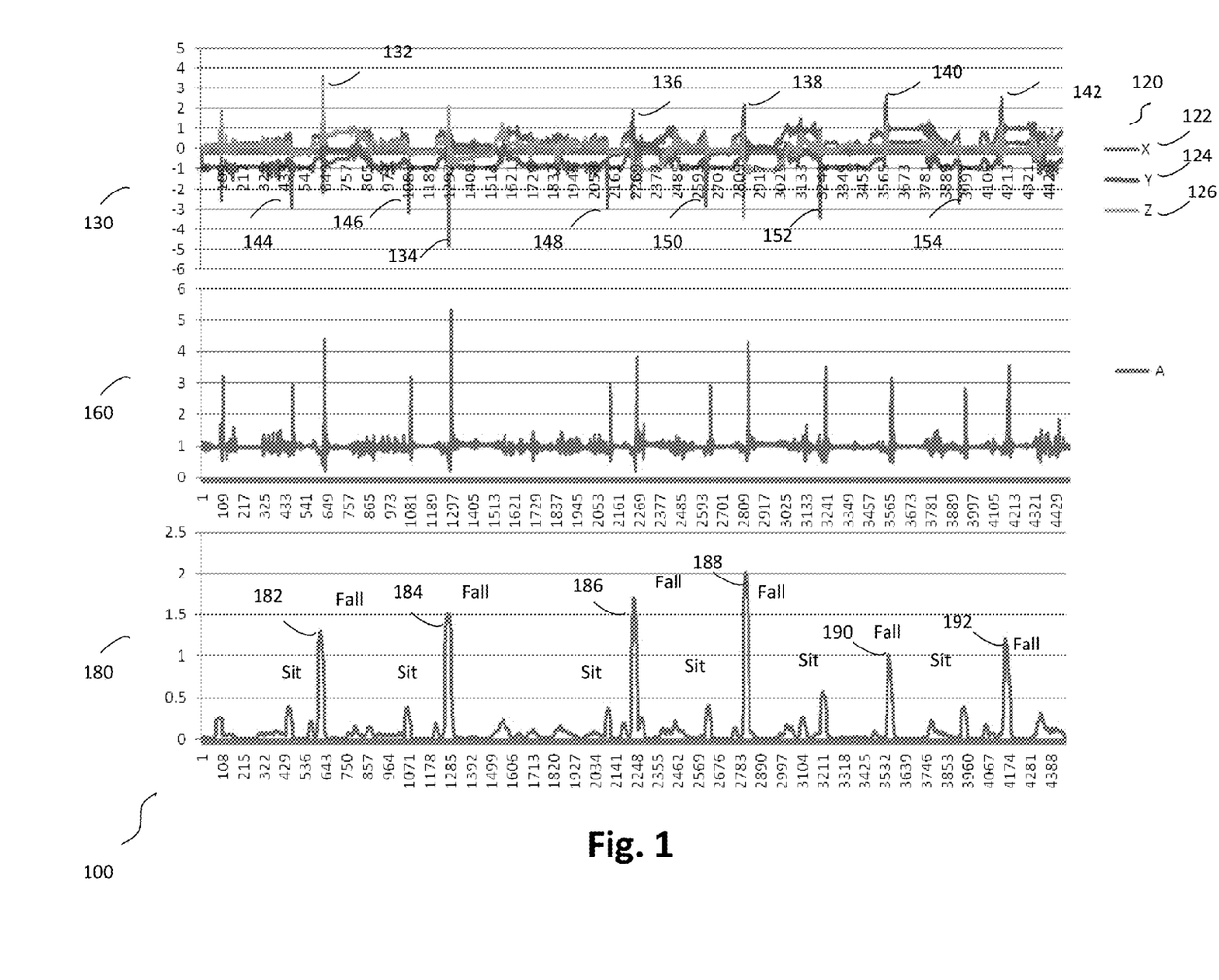
FIG. 1 is a set of graphs showing acceleration data and amplitudes of received, processed, and filtered data.

FIG. 1 is a set of graphs (100) showing acceleration data acquired from an accelerometer attached to a body while a person was walking, sitting into a chair, falling and getting up. The set of graphs illustrate raw acceleration data, processed acceleration data, and filter impact features pertaining to the processed acceleration data. In the example reflected in the graphs, the body has at least one tri-axis sensor for sensing acceleration data on the x-axis (122), y-axis (124), and z-axis (126), as reflected in the legend (120). In the example shown herein, raw acceleration data is acquired from the sensor across each of the represented axis. Accordingly, the graphs reflect movement of the body to which the sensor is attached.

The first of the three graphs, (130), illustrates acceleration data provided by the sensor when the body to which the sensor is attached is subject to movement. As shown, the acceleration data has significant peaks (132)-(142), and insignificant peaks (144)-(154). In one embodiment, significant peaks pertain to signal data with a strong amplitude, and insignificant peaks pertain to signal data with a low amplitude, with each of the peaks separated with noise. In one embodiment, a signal processing algorithm identifies values of the signal amplitudes. Since the data shown in graph (130) is raw, the data must be processed to learn the true nature and identify of the data.

The second of the three graphs, (160), illustrate the raw data following a first set of processing. More specifically, the acceleration data shown herein is represented as a magnitude of an acceleration vector, A, wherein the acceleration magnitude is taken based upon the following mathematical formula:

$$A = SQRT(X^2 + Y^2 + Z^2)$$

with X, Y, and Z acceleration magnitudes associated with x, y, and z axis. As shown, the peaks from the raw acceleration data are more prevalent in graph (160) in comparison to graph (130), with the non-peak segments minimized. Accordingly, by converting the raw acceleration data with respect to the x, y, and z axis resulting vector magnitude representation, which represent specific actions, are more pronounced.

The third of the three graphs, (180), illustrates data from both the raw acceleration data of the first graph (120) and resulting vector magnitude data of the second graph (160), after the data has been filtered. More specifically, and as illustrated in detail below, the vector data is statistically and spatially filtered to extract impact features associated with the sensor data. As shown herein, the peaks are further accentuated or less accentuated from the vector representation. More specifically, the acts of sitting and falling are more clearly pronounced. The fall data is shown at (182)-(192), with all of the other less significant peaks and acceleration data represented as acts of sitting. Accordingly, changes of data associated with accelerometer readings take place as the body moves between sitting and falling positions.

Figure 2:
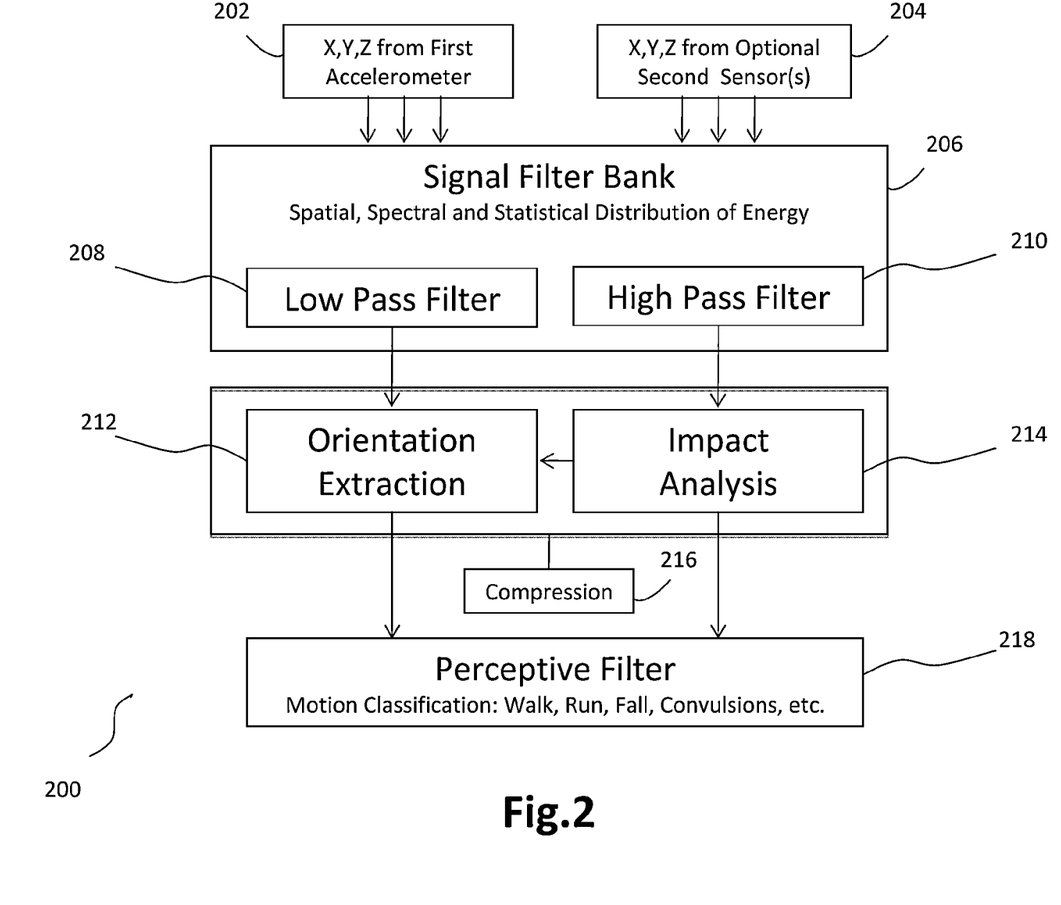
FIG. 2 depicts a process and architecture for fall detection.

As shown in FIG. 1, patterns of data may be studied to understand how acceleration data is affected by movement of a sensor attached to a body. The patterns may be applied to movement of the body in real-time application thereof. FIG. 2 is a flow diagram (200) illustrating a process for extracting and processing signal features so that they may be evaluated for real-time or near-real-time application. Initially, sensor data is obtained from the sensor (202). In one embodiment, the sensor is attached directly to the body of the user. Similarly, in another embodiment, the sensor is indirectly attached to the body of the user. The sensor may come in different forms to acquire different categories of data. As shown at (202), the sensor is a tri-axis accelerometer, although the invention should not be limited to this particular embodiment. Optionally, the device may include one or more secondary sensors (204). The secondary sensors may include one or more of a tri-axis accelerometer, a magnetometer, a compass, etc. It should be noted that use of two accelerometers requires both of the accelerometers to be rigidly mounting to the device, whereas use of a secondary sensor in the form of a pressure sensor does not require rigid mounting to the device. Following gathering of the sensor data at step (202) and/or (204), the obtained data is applied to a signal filter bank (206). As shown herein, the filter bank (206) is configured with at least one low pass filter (208) and at least one high pass filter (210). The quantity of filters shown herein is for illustrative purposes, and the invention should not be limited to this illustrated quantity. High pass filter data is forwarded to the high pass filter (210) and low pass filter data is forward to the low pass filter (208). Low pass filter data includes orientation data. As such, the low pass filter (208) is applied to extract orientation data from the accelerometer (212), and in one embodiment may also extract data pertaining to gravity and/or magnetic field, depending on the use and form of the associated secondary sensors. The high pass filter (210) is applied to extract data pertaining to impact from one or more secondary sensors (214), including but not limited to magnitude and energy of impact, and noise.

Following statistical processing of the data, the statistical data is compressed (216), employing one or more known data compression techniques. Two different compression techniques are described below. However, in one embodiment, alternative or additional compression techniques may be employed. Both of the compression techniques are employed to reduce signal processing data, and include a stepping window algorithm and a sliding window algorithm. The stepping algorithm employs a stepping window technique wherein statistical properties of the data are extracted within the window and adjacent time segments to sample sensory data are processed. The following is a formula for a stepping window algorithm:

$$Ws=A[i+(s-1)*w]:A[i+s*w-1],$$

where Ws is the window, w is the number of samples in the window, s is the step number, and A is the sensor data, including but not limited to data from an accelerometer, a magnetometer, a pressure sensors, etc. In one embodiment, the filter bank accepts data from any sensor in communication with the device. Furthermore, in one embodiment, a sliding window technique may be employed in addition to the stepping window technique, or in place thereof. The sliding window algorithm extracts statistical properties of the data within the window, and averages features of data over time. The following is a formula for a sliding window algorithm:

$$Wp=SP[i]:SP[i+k],$$

where SP is a statistical property, such as a window average, variance, etc., k is the number of samples in the window and i is the number of the sample. However, in contrast to the stepping window algorithm, there is an overlap of adjacent time segments in the sliding window algorithm. As shown herein data is obtained from the sensor(s) and dissected to extract feature data associated with orientation towards gravity. Each of the high and low pass filters is associated with a portion of the frequency spectrum. Accordingly, for each of the high and low pass filters, data associated with orientation and/or impact is extracted and processed in the form of spatial, spectral and statistical distribution of energy.

Figure 4:
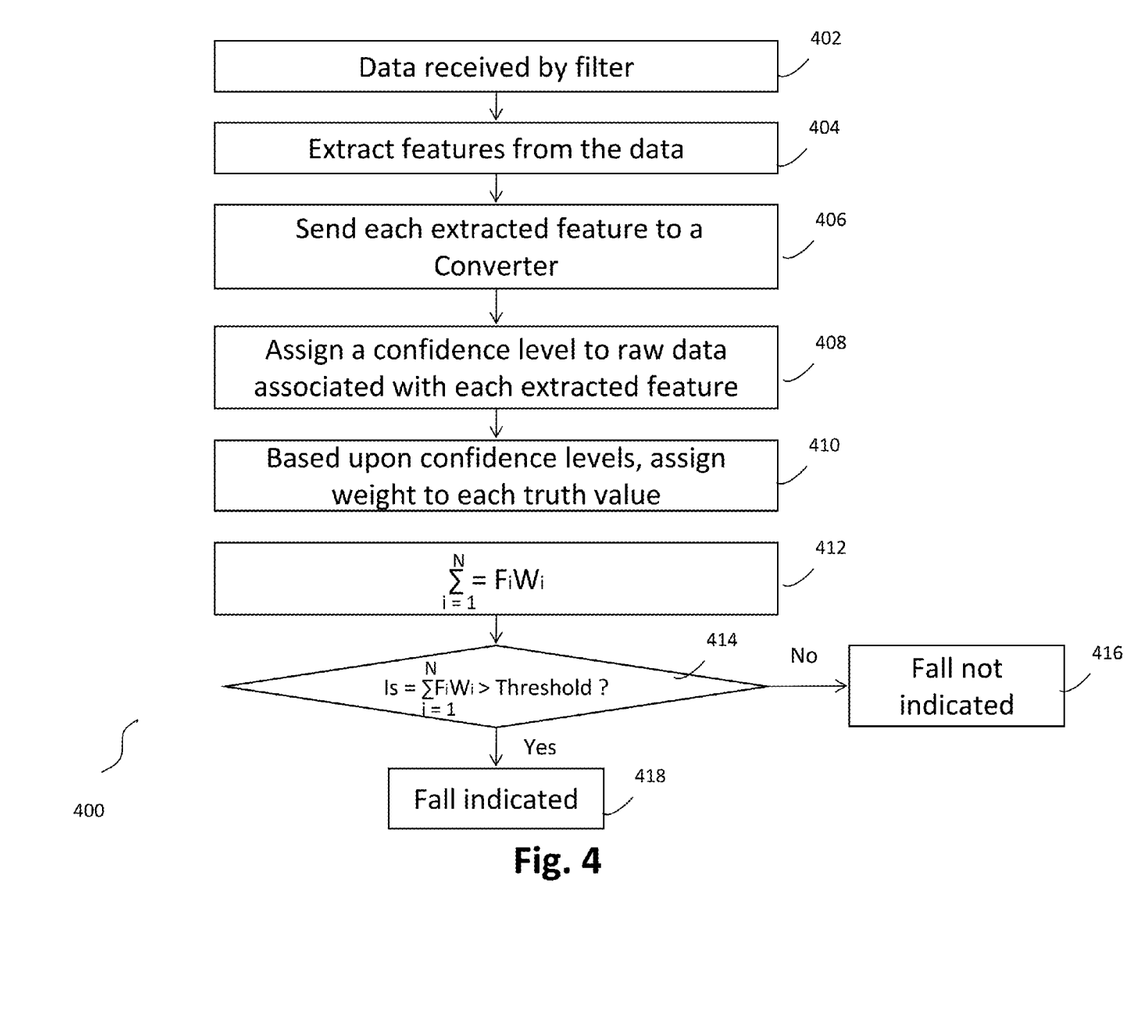
FIG. 4 depicts filtering extracted signal data for conversion of the extracted data to truth values to then enable the proper classification to real world properties.

As shown, in the filter bank (206), the data is processed to gather orientation data (212) and to analyze impact data (214). More specifically, with respect to the impact analysis different types of statistics may be gathered within a time window from the filtered data, including but not limited to, average, variance, noise, range, standard deviation, magnitude of impact, etc. In one embodiment, the statistics are computed for each of the axis components associated with the sensor. Following statistical processing of the data and for each set of analyzed data, the data is compressed (216) and forwarded to a filter (218) to determine perceptive analysis of the data. The filter (218) classifies the received data. Details of the filter are shown in FIG. 4. Accordingly, as shown herein data is obtained from the sensor(s) and dissected to extract statistical orientation data associated with the acceleration and/or impact.

Figure 3:
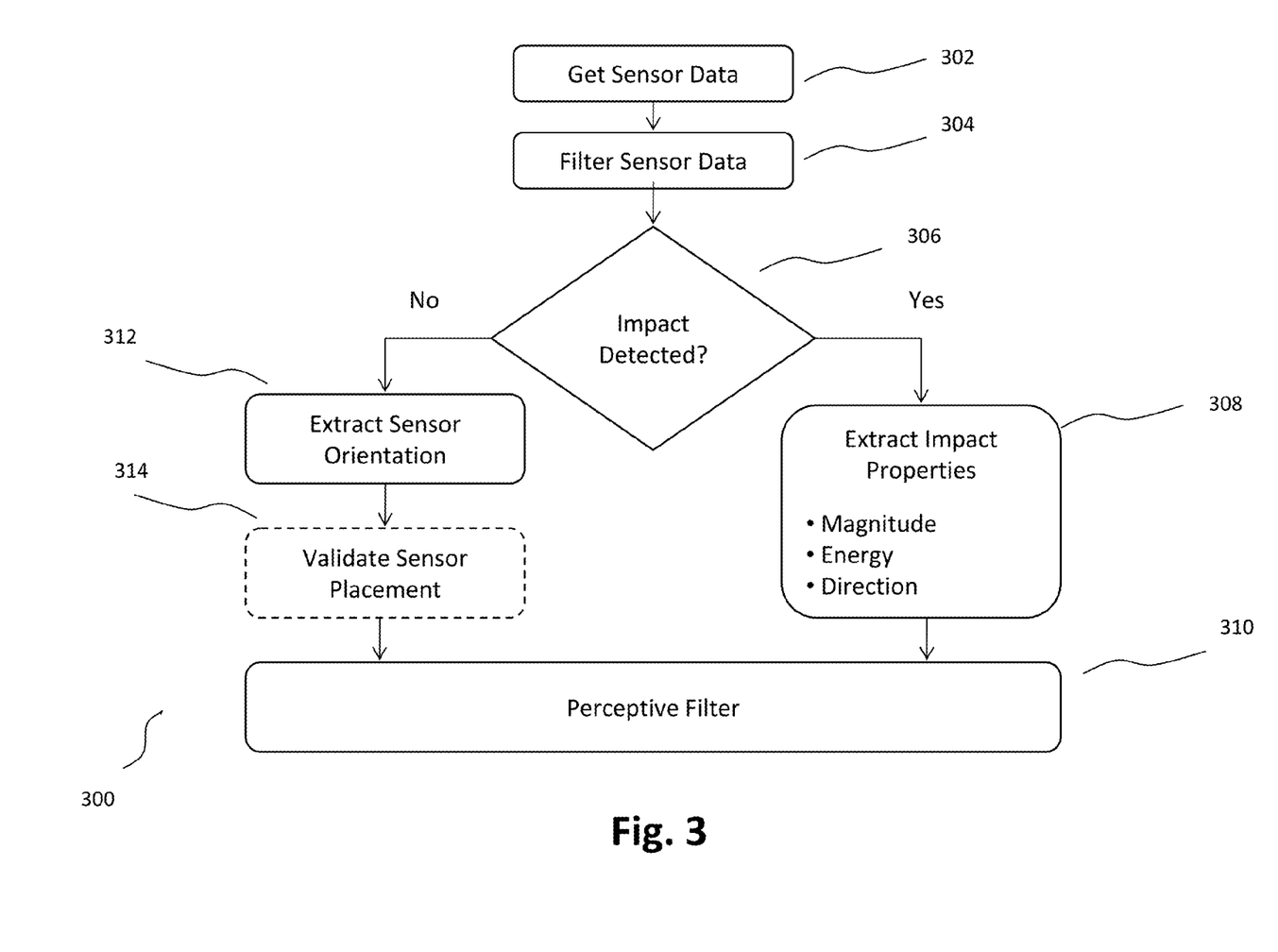
FIG. 3 depicts a flow chart of a fall detection activity diagram.

FIG. 2 as described above illustrates the architecture of the fall detection algorithm. To further illustrate the process of detecting a fall, FIG. 3 is provided in the form of a flow chart (300) illustrating the steps for detecting an actual fall of the sensor attached to the body. Initially, sensor data is obtained from the accelerometer and any other secondary sensors attached to or in communication with the body (302). In one embodiment, the sensor is configured with at least one tri-axis accelerometer which is attached to the body, and at least one secondary sensor in a different form which is in communication with the body. Following gathering of the sensor data at step (302), the obtained data is applied to a filter (304). As shown in FIG. 2, the filter includes a filter bank configured with at least one high pass filter and at least one low pass filter. In one embodiment, the filter bank may include more than one high pass and/or low pass filters. The quantity of filters shown herein is for illustrative purposes, and the invention should not be limited to this illustrated quantity. Each set of high and low pass filters is associated with a portion of the frequency spectrum. The frequency spectrum is segmented, with each segment having a set of filters.

Following the filtering of the data in the filter bank (304), the data is processed to determine if an impact has been extracted (306). In one embodiment, the determination at step (306) may be replaced with the positive affect of determining an impact and processing the data in response thereto. If an impact has been determined, properties pertaining to the impact are extracted from the sensor(s) (308). In one embodiment, impact properties include, but are not limited to, magnitude, energy, direction, and rotation of the body. Following step (308), the extracted data is forwarded to a filter (310) for classifying the data associated with the fall. Details of the filter are shown in FIG. 4.

Conversely, if at step (306) it is determined that an impact has not been detected from the filtered data, the orientation data of the body as acquired from the sensor is extracted (312). In one embodiment, the true vertical of the body may be ascertained in real-time as the body to which the sensor is attached is in motion. What is considered to be vertical may differ from person-to-person, or among object placements. An algorithm for learning the true vertical is shown in detail in FIG. 6. If the true vertical is being ascertained, data associated with the true vertical is forwarded to the perceptive filter (310). Another option following step (312) is to validate placement of the sensor (314). Sensor placement may include, but is not limited to, attachment of the sensor to the body. If the sensor is attached to the body there will be certain noise associated therewith, and if the noise is not detected then there is specific data that may be indicative of a device being dropped. Both forms of noise data are forwarded to the perceptive filter (310). Accordingly, as shown herein data is obtained from the sensor(s) and dissected to extract orientation and impact data associated with detection of a fall.

As noted above, the orientation and/or impact data is forwarded to a perceptive filter to determine whether or not the orientation data is characteristic of a fall. FIG. 4 is a flow chart (400) illustrating an algorithm employed by the perceptive filter. In one embodiment, the perceptive filter is invoked at such time as a high frequency variance is exceeded. As the data is received by the filter (402), for each data received features are extracted from the data (404), where N represents the quantity of extracted features. In one embodiment, extracted features include, but are not limited to, noise, magnitude, and impact. Data associated with each extracted feature is sent to a converter to convert the data to a scale value (406). More specifically, at step (406) the conversion is employed to ascertain whether the data values are weak or strong relative to objective data. In one embodiment, the conversion applies a truth value to data associated with each extracted feature. Details of the truth value conversion and scale are described below with respect to FIG. 5. In one embodiment, a high truth value is assigned to a feature with a strong characteristic, and a low truth value is assigned to a feature with a low characteristic. Following the conversion to truth values at step (406), a confidence level is assigned to raw data associated with each extracted feature (408). The confidence level assignment is a measure of reliability of the raw data. In one embodiment, a scale is provided for assignment of confidence levels to the raw data. Based upon the confidence levels, a weight, W, is assigned to each truth value (410). In one embodiment, each weight is mathematically applied to each truth value. Similarly, in one embodiment, one or more of the weights are static. In another embodiment, one or more of the weights are dynamic and may be modified in real-time. Regardless of the static or dynamic value assigned to the weight, the result of applying the weight to the truth value is a numerical weight value, W. Following step (410), a summation of the quantity of features, F, and weights, W, is calculated over a period of time segmented into before impact, impact, and after impact (412) as follows:

$$\sum_{i=1}^{N} = F_i W_i$$

where N represents the quantity of features being evaluated, F is the feature extracted by the filter, and W is the weight assigned to the truth value of the feature based upon the confidence level. It is then determined if the value of the summation exceeds a threshold (414). A positive response to the determination at step (414) is an indication that a fall has been detected (418). Conversely, a negative response to the determination at step (414) is an indication that a fall has not been detected (416). Accordingly, the perceptive filter shown here is a filter to provide fall detection and motion classification based upon truth values and confidence levels of the raw data.

Figure 5:
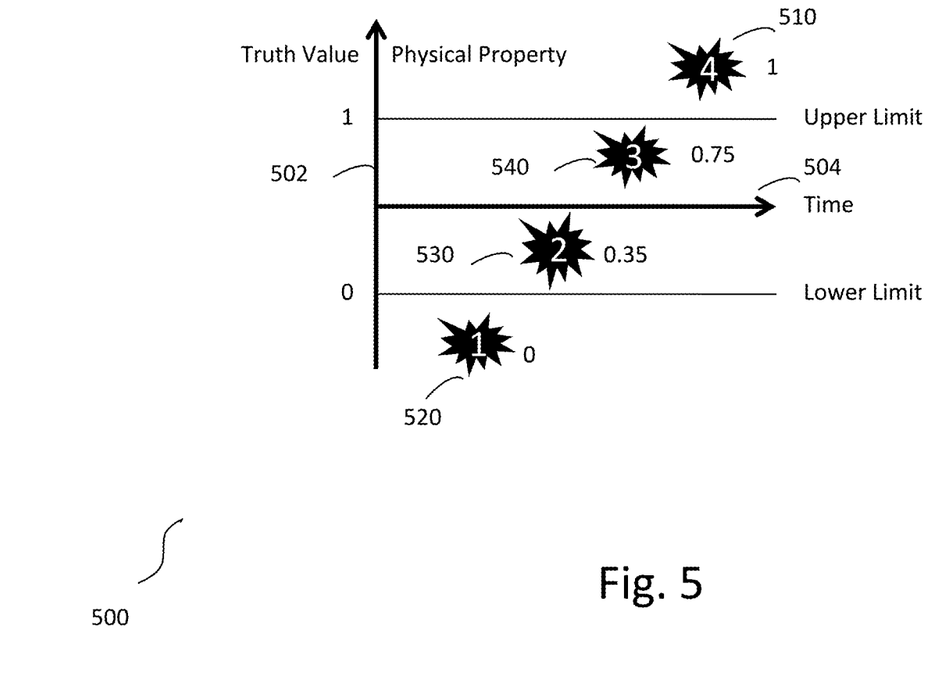
FIG. 5 depicts a truth value scale.

As described in the perceptive filter of FIG. 4, truth values are assigned to each of the extracted features. More specifically, prior to the translation to an objective property, the statistical data is converted to a truth value. The truth value is a numerical value on a scale of values. In one embodiment, the scale ranges from zero to one, with one representing a strong value and zero representing a weak value, although the invention should not be limited to this embodiment. FIG. 5 is a graph (500) illustrating a truth value scale. As shown in this example, the truth values are represented on one of the axis (502), with time represented on another axis (504). A maximum truth value (510) is shown at maximum position on the scale, and a minimum truth value (520) is shown at a minimum position on the scale. Two other truth values (530) and (540) are shown on the scale, with (530) representing a truth value closer to the minimum limit (520), and (540) representing a truth value closer to the maximum limit (510). In one embodiment, the truth values may be applied across a different scale, an inverted scale, a circular scale, etc., and as such, the invention should not be limited to the particular embodiment of the truth value scale shown herein. Accordingly, as shown in FIG. 5, a truth scale is provided to apply the statistical data to an objective property.

Figure 6:
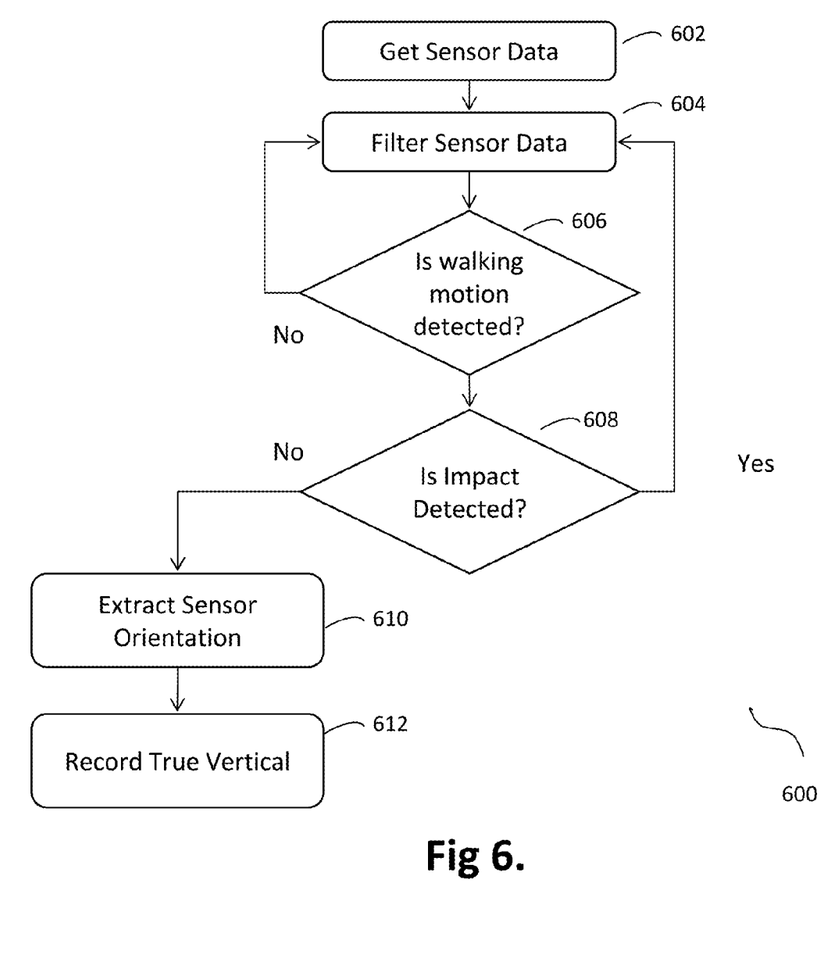
FIG. 6 depicts a flow chart for learning true vertical activity.

As described above, the body is provided with at least one accelerometer attached to the body. In one embodiment, the accelerometer is fixed to the body. Based upon the relationship of the accelerometer to the body, orientation data may be evaluated from data acquired from the accelerometer. In order to determine whether or not there has been an impact associated with the fall, the vertical position of the body and associated sensor data must be ascertained. In one embodiment, a true vertical position of the body may be acquired and employed in place of the vertical measurement of the sensor data. FIG. 6 is a flow chart (600) illustrating a process for learning the true vertical value of the sensor prior to impact. At such time as the body to which the sensor is attached is subject to movement, sensor data is acquired (602). In one embodiment, the acquisition of sensor data is triggered by movement. For each acquired data value, the sensor data is filtered (604) and then subject to a determination of a walking motion (606). In one embodiment, the determination at step (606) looks at the pattern of the acceleration data for motion. When a person walks, their body is in an erect or semi-erect position. A negative response to the determination at step (606) is followed by a return to step (604). Conversely, a positive response to the determination at step (606) is followed by determining whether a disruption of the periodic pattern has been detected (608). In one embodiment, the disruption detection at step (608) is an indication of an impact. A disruption may include a strong magnitude followed by a low magnitude, or a change in the pattern of the signal.

A positive response to the determination at step (608) is followed by a return to step (604). Conversely, a negative response to the determination at step (608) is followed by extracting sensor orientation data (610) and recording the extracted sensor orientation data as the true vertical position of the body (612). In one embodiment, the ascertainment of the true vertical of the body continues every time the person in communication with the sensor is moving. As such, following step (612), the process continues with a return to step (602).

Accordingly, the true vertical learning process is triggered with motion of the sensor and may continue as long as the sensor is subject to motion.

Data evaluation is divided into three segments, before impact, impact, and after impact. The true vertical evaluation of the sensor may be employed for both the before and after impact segments. More specifically, by acquiring the true vertical of the body, the evaluation and detection of an actual fall may be accurately defined.

As will be appreciated by one skilled in the art, aspects of the present invention may be embodied as a system, method or computer program product. Accordingly, aspects of the present invention may take the form of an entire hardware embodiment, an entire software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described above with reference to a flowchart illustration and/or block diagrams of methods, apparatus (systems) and computer program products according to embodiments of the invention. It will be understood that each block of the flowchart illustration and/or block diagrams, and combinations of blocks in the flowchart illustration and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Figure 7:
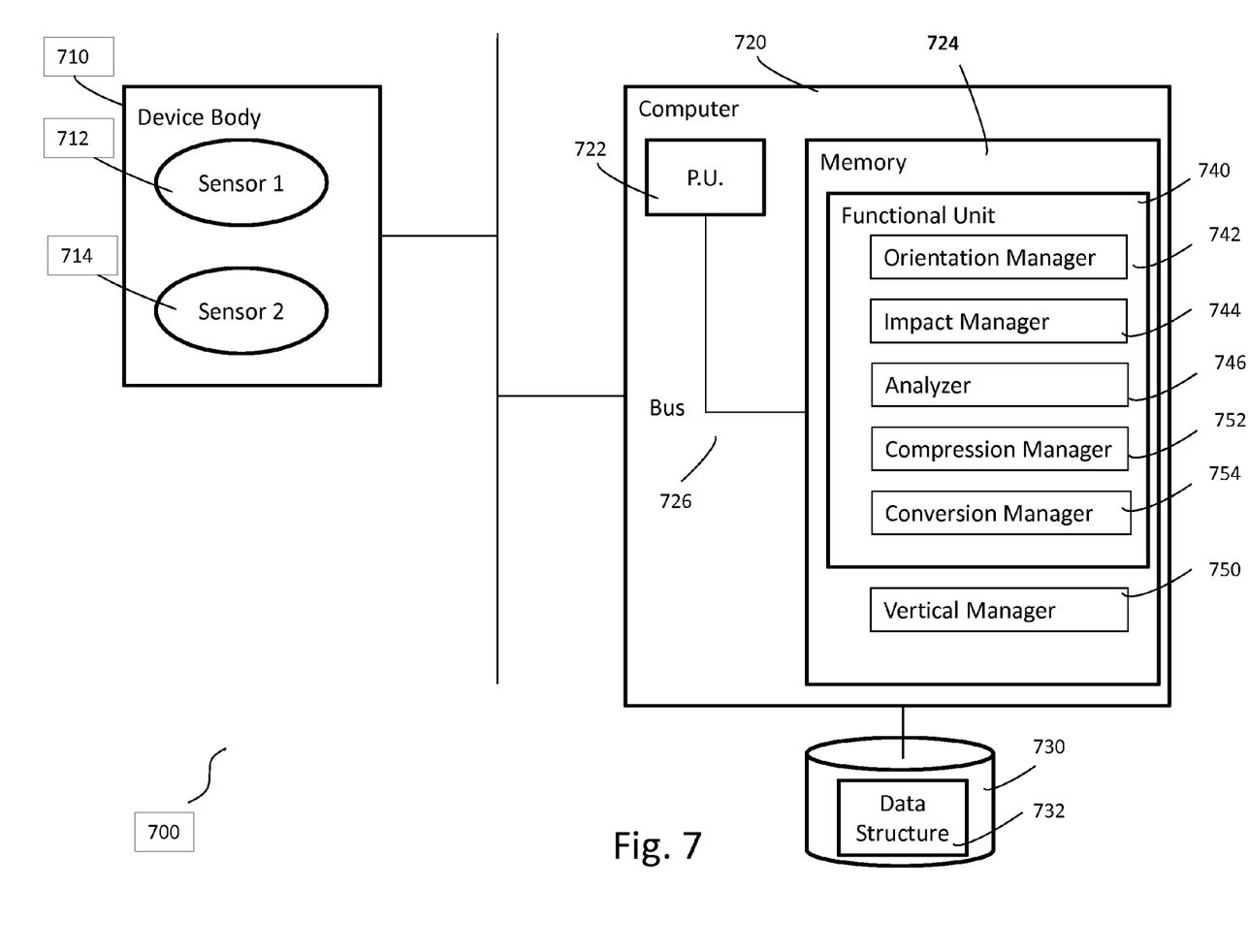
FIG. 7 depicts a block diagram illustrating tools to support fall detection of a body in communication with a sensor.

Referring now to FIG. 7 is a block diagram (700) showing a system for implementing an embodiment of the present invention. The system includes a device body (710) in communication with a computer (720). The device body (710) is provided with a sensor (712) to generate motion signals when subject to motion. In one embodiment, the sensor (712) is a tri-axis accelerometer. The device body (710) communicates the motion signal to the computer (720), which is configured with a processing unit (722) in communication with memory (724) across a bus (726), and data storage (730).

There are different tools employed to support derivation of placement information for the device body (710). For purposes of illustration, the tools will be described local to the computer (720). In one embodiment, the tools may be local to the device body (710). A functional unit (740) is provided in communication with the sensor (712) to provide the tools to analyze a change in orientation of the body (710). In one embodiment, the functional unit is referred to as a fall detection tool, and may be used herein interchangeably. More specifically, the functional unit (740) includes an orientation manager (742), an impact manager (746), and an analyzer (752). The orientation manager (742) determines orientation data as derived from acceleration data received from the sensor (712). The impact manager (746), which is in communication with the orientation manager (742), determines impact data as derived from acceleration data received from the sensor (712). The analyzer (752) separates a time segment associated with impact into at least three distinct and sequential time segments. These segments include a before impact segment, an impact segment, and an after impact segment. In one embodiment, the before and after impact segments extract orientation of the sensor, and the impact segment extracts properties of the impact, including but not limited to magnitude, energy, high frequency energy, rotation, direction, and attachment to the body. The analyzer (752) analyzes a change in the orientation of the body towards gravity from the before impact segment to the after impact segment. In one embodiment, the change employed by the analyzer includes a difference in orientation between these two segments. Accordingly, the evaluation of orientation with respect to the segmented time block enables orientation to be analyzed in a granular fashion.

As described herein, time is divided into three segments to provide a granular approach to sensor data evaluation and fall detection. As shown above in FIG. 1, the raw acceleration data is converted into resulting vector data. The variable N represents the quantity of vector samples in both the before and after impact segments, and the variable M represents the quantity of vector sample in the impact segment. The variable A represents a three dimensional vector with spatial components along the x, y, and z axis. The following formula may be employed to calculate body orientation towards gravity on the before impact segment:

$$OBI=\text{Average}(A[i]:A[i+N-1])$$

where i is the first sample data, i+N−1 is the last sample data in the before impact segment, A[i] is the acceleration sample at the beginning of the before impact segment, and A[i+N−1] is the acceleration sample at the end of the before impact segment.

The following formula may be employed to calculate body orientation towards gravity on the after impact segment:

$$OAI=\text{Average}(A[i+N+M]:A[i+2N+M])$$

where i+N+M is the first sample data in the after impact segment, i+2N+M is the last sample data in the after impact segment, A[i+N+M] is the acceleration sample at the beginning of the after impact segment, and A[i+2N+M] is the acceleration sample at the end of the before impact segment.

As noted above, an impact manager (744) is provided to extract impact data from the sensory Data. The following formula may be employed by the impact manager (744) to calculate the energy of the impact:

$$EI=\text{Variance}(A[i+N]:A[i+N+M])$$

where i+N is the first sample data in the impact segment, and i+N+M is the last sample data in the impact segment, A[i+N] is the acceleration sample at the beginning of the impact segment, and A[i+N+M] is the acceleration sample at the end of the impact segment.

The following formula may be employed by the impact manager (744) to calculate the magnitude of the impact during the impact segment:

$$MI=\text{Maximum}(A[i+N]:A[i+N+M])$$

where i+N is the first sample data in the impact segment, and i+N+M is the last sample data in the impact segment, A[i+N] is the acceleration sample at the beginning of the impact segment, and A[i+N+M] is the acceleration sample at the end of the impact segment.

The following formula may be employed by the impact manager (744) to calculate the high frequency energy of the impact during the impact segment:

$$HEI=\text{Average}((A[i+N]-A[i+N+1]):(A[i+N+M-1]-A[i+N+M]))$$

The following formula may be employed by the impact manager (744) to calculate the direction of the impact:

$$DI=A\max(X,Y,Z)$$

To provide resolution between a fall and a device drop, the attachment of the sensor to the body can be detected by one or more proximity sensors, such as accelerometers, to sense attachment noise produced by the body. The following formula may be employed by the impact manager (744) to calculate attachment noise $$\text{Attachment Noise}=\text{sum}((X[i+N+1]-(X[i+N]+X[i+N+2])/2:X[i+N+M]-(X[i+N+M-1]+X[i+N+M+1])/2]))$$

where i, N, and M are defined above, and wherein X is the acceleration data along the x-axis as obtained from the accelerometer.

As described above, the sensor (712) is in the form of an accelerometer. In one embodiment, a second sensor (714) may be provided in the form of a second accelerometer attached to the body (710), and also in communication with the functional unit (740). With the use of a second accelerometer, the functional unit (740) is configured to extract rotation data associated with the impact segment. In one embodiment, the rotation is an integrated vector cross product within the impact segment. Similarly, in another embodiment, a magnetic vector, a motion vector, or a differential signal between the two accelerometers may be used to extract rotation data. The following are examples of formulas employed for calculating rotation:

$$\text{Rotation during Impact}=\text{Average}((A[i+N]*A[i+N+1]/|A[i+N]|*|A[i+N+1]|):(A[i+N+M-1]*A[i+N+M]/|A[i+N]|*|A[i+N+1]|)),$$

where the product of the vectors is a dot product or $$\text{Rotation during Impact}=\text{Average}((A1[i]-A2[i]):(A1[i+N-1]-A2[i+N-1]))$$

where A1 and A2 are motion vectors from the first and second accelerometers.

Conversely, the rotation during an impact can be also ascertained with a magnetometer. The following formula is an example of calculating rotation during impact from data received from a magnetometer:

$$\text{Rotation}=\text{Variance}(H[i+N]:H[i+N+M]),$$

where H is a magnetic field vector.

The attachment noise shown herein is calculated based upon noise received from the sensor (712) in the form of an accelerometer. The attachment noise can be extracted by any known curve smoothness filters. Furthermore, in each of the calculation shown herein, the impact manager (744) monitors an impact of the body within an impact detection time window based upon data from an accelerometer.

In one embodiment, the second sensor (714) may be a pressure sensor. The impact manager (744) detects altitude and air pressure in both the before impact segment and the after impact segment, and compares the difference to a threshold. Similarly, in one embodiment, the second sensor (714) may be a microphone. The impact manager (744) cross-correlates a signal from the microphone with an impact signal. More specifically, if the maximum value of the microphone signal occurs at the same time as a maximum impact, then the probability of impact increases.

In addition to the tools described above, a vertical manager (750) is provided in communication with the functional unit (740). In one embodiment the vertical manager (750) can be embodied within the functional unit (740). The vertical manager (750) is employed to acquire sensor data from the sensor (712) and to learn the true vertical value of the sensor before impact. Details showing the algorithm for calculating the true vertical value are shown in FIG. 6 described above. The vertical manager (750) replaces the prior vertical value of the before impact segment with the true vertical value. Accordingly, the vertical manager supports determination of a fall by replacement of a vertical value provide by the accelerometer with the true vertical value associated with the sensor while subject to movement before impact.

As shown in FIG. 2, data is acquired and processed through a signal filter bank, and thereafter subject to statistical processing and compression. To support the data compression, a compression manager (752) is provided in communication with the analyzer (746). More specifically, the compression manager computes and compresses statistical data received from the sensor (712) over time. Different compression techniques may be implemented, including but not limited to, a stepping window and a sliding window. The stepping window technique extracts statistical properties of the data within the window to sample sensory data are processed. In one embodiment, a sliding window technique may be employed in addition to the stepping window technique, or in place thereof. The sliding window technique extracts statistical properties of the data within the window, and averages features of data over time. However, in contrast to the stepping window technique, there is an overlap of adjacent time segments. Accordingly, as shown herein data is obtained from the sensor(s), processed, and compressed with respect to time.

As described above with respect to FIG. 5, truth values may be assigned to objective properties of the signal. In one embodiment, to support the data conversion to truth values, a conversion manager (754) is provided in communication with the analyzer (746). More specifically, the conversion manager (754) assigns truth value to the objective properties and assigns a weight to each objective property. The conversion manager (754) may pass the weighted data to fall detection and motion classification logic. In one embodiment, the logic is a data structure (732) stored in data storage (730) in communication with the functional unit, where weighted data is charted against fall determination data. The following is a formula that may be used by the data logic to determine whether to pass the weighted data:

$$IF(\text{sum}(OP1*W1:OPn*Wn))>Tf), \text{then Fall}$$

where OPn is an objective property, Wn is a weight, and Tf is a threshold.

As identified above, the functional unit and the tools and managers embedded therein are shown residing in memory of the machine in which they reside. As described above, in different embodiment the functional unit and the tools and managers may reside on different machines in the system. In one embodiment, the functional unit and the tools may reside as hardware tools external to memory of the machine in which they reside, or they may be implemented as a combination of hardware and software. Similarly, in one embodiment, the functional unit and the tools may be combined into a single functional item that incorporates the functionality of the separate items. As shown herein, each of the functional unit and the tools are shown local to one machine. However, in one embodiment they may be collectively or individually distributed across the pool of configurable computer resources and function as a unit to manage dynamic data evaluation and fall detection. Accordingly, the functional unit and the tools may be implemented as software tools, hardware tools, or a combination of software and hardware tools.

The flowcharts and block diagrams in the Figures illustrate the architecture, functionality, and operation of possible implementations of systems, methods and computer program products according to various embodiments of the present invention. In this regard, each block in the flowcharts or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

It will be appreciated that, although specific embodiments of the invention have been described herein for purposes of illustration, various modifications may be made without departing from the spirit and scope of the invention. Accordingly, the scope of protection of this invention is limited only by the following claims and their equivalents.

I claim:

1. A system comprising:
a sensor attached to a body;
the sensor to acquire sensory data, including acceleration data, and
a tool to detect fall of the body in accordance with the acquired sensory data, the tool comprising:
an orientation manager to extract orientation data from the acquired sensory data;
an impact manager to quantitatively compute cumulative high frequency energy of impact data from the acquired sensory data; and
an analyzer to analyze the orientation data and the impact data and to detect a fall, including the analyzer to differentiate the detected fall from an intentional change of posture, including weighting acceleration data extracted from the sensor, the extracted data including impact, orientation, and energy.

2. The system of claim 1, further comprising a vertical manager in communication with the fall detection tool, the vertical manager to learn a true vertical value of the sensor before impact, and to replace a prior vertical value of a before impact time segment with the true vertical value.

3. The system of claim 1, further comprising a compression manager in communication with the analyzer, the compression manager to compute and compress statistical data over time received from the acquired sensory data, the tool including a technique selected from the group consisting of: a stepping window and a sliding window.

4. The system of claim 3, wherein the stepping window technique extracts statistical properties of data within a stepping window and includes a processing of adjacent time segments to sample sensory data.

5. The system of claim 3, wherein the sliding window technique extracts statistical properties of data within a sliding window and includes an overlap of adjacent time segments to average features of the data over time, wherein each average comprises features of the data from impact segments in the adjacent time segments.

6. The system of claim 1, further comprising the impact manager to monitor an impact of the body within an impact time segment, including monitoring for a parameter reflective of cumulative energy of a sensory signal within the segment to exceed a threshold.

7. The system of claim 1, wherein before and after the orientation data extractions are conducted from the sensory data before and after impact time segments, and the cumulative high frequency energy is computed during an impact time segment.

8. The system of claim 1, further comprising the impact manager to provide resolution between a fall and a device drop by detection of attachment of the sensor to the body.

9. The system of claim 1, further comprising a secondary sensor attached to the body, the secondary sensor being a second accelerometer, the secondary sensor in communication with the tool, wherein the tool extracts rotation data associated with an impact time segment.

10. The system of claim 1, further comprising a secondary sensor attached to the body, the secondary sensor being a compass, the secondary sensor in communication with the impact manager, the impact manager to extract magnetic field data associated with the detected fall.

11. The system of claim 1, further comprising the impact manager to extract rotation data using a differential signal from two tri-axis accelerometers, and to determine excessive rotation within an impact time segment.

12. The system of claim 11, further comprising a secondary sensor in the form of a pressure sensor, and the impact manager to extract altitude data from the secondary sensor, including a change in altitude from a before impact time segment and an after impact time segment.

13. The system of claim 1, further comprising a secondary sensor in the form of a microphone, the impact manager to acquire sound data from the microphone during an impact time segment.

14. The system of claim 1, further comprising a conversion manager to convert and weight physical signal properties, including assignment of truth values to objective properties, and assignment of a weight to each objective property.

15. The system of claim 1, further comprising a secondary sensor attached to the body, the secondary sensor in the form of a proximity sensor, and the impact manager to detect if the secondary sensor was on a user during an impact time segment to differentiate a device drop from a human fall.

16. A method comprising:
providing a processing unit in communication with memory and a data structure to store sensory data, the processing unit to process the sensory data;
receiving the sensory data from a sensor attached to a body in communication with the processing unit, the sensory data including acceleration data;
detecting fall of the body in accordance with the acquired sensory data, including:
extracting orientation data from the acquired sensory data; and
quantitatively computing cumulative high frequency energy of impact data from the acquired sensory data; and
analyzing orientation data and impact data and detecting a fall, including differentiating the detected fall from an intentional change of posture, including weighting acceleration data extracted from the sensor, the extracted data including; impact, orientation, and energy.

17. A computer program product for use with a sensor attached to a body, the sensor to acquire sensory data, the computer program product comprising a non-transitory computer readable storage medium having computer readable program code embodied thereon, which when executed causes a computer to implement the method comprising:
receiving sensory data from a sensor attached to a body, the sensory data including acceleration data;
detecting fall of the body in accordance with the acquired sensory data, including:
extracting orientation data from the acquired sensory data; and
quantitatively computing cumulative high frequency energy of impact data from the acquired sensory data; and
analyzing orientation data and impact data and detecting a fall, including differentiating the detected fall from an intentional change of posture, including weighting acceleration data extracted from the sensor, the extracted data including impact, orientation, and energy.

18. The computer program product of claim 17, further comprising learning a true vertical value of the sensor before impact, and to replace a prior vertical value of a before impact time segment with the true vertical value.

19. The computer program product of claim 17, further comprising computing and compressing statistical data over time received from the acquired sensory data, including a technique selected from the group consisting of: a stepping window and a sliding window, wherein the stepping window technique extracts statistical properties of data within a stepping window and includes a processing of adjacent time segments to sample sensory data and the sliding window technique extracts statistical properties of data within a sliding window and includes an overlap of adjacent time segments to average features of the data over time.

20. The computer program product of claim 17, further comprising monitoring an impact of the body within an impact time segment, including monitoring for a parameter reflective of cumulative energy of a sensory signal within the time segment to exceed a threshold.

21. The computer program product of claim 17, wherein before and after the orientation data extractions are conducted from the sensory data before and after impact time segments, and the cumulative high frequency energy is computed during an impact time segment.

* * * * *